(12) United States Patent
Michalek et al.

(10) Patent No.: US 9,149,554 B2
(45) Date of Patent: Oct. 6, 2015

(54) METHOD AND APPARATUS FOR TREATING WASTE INVOLVING CONTROL OF ENERGY INPUT TO ASSURE STERILIZATION

(75) Inventors: Jan K. Michalek, Pataskala, OH (US); Theodore J. Thomas, Columbus, OH (US); Leong Soon Lee, Columbus, OH (US)

(73) Assignee: Estech USA, LLC, Canal Winchester, OH (US)

( * ) Notice: Subject to any disclaimer, the term of this patent is extended or adjusted under 35 U.S.C. 154(b) by 306 days.

(21) Appl. No.: 12/691,124

(22) Filed: Jan. 21, 2010

(65) Prior Publication Data
US 2010/0200683 A1 Aug. 12, 2010

Related U.S. Application Data
(60) Provisional application No. 61/205,632, filed on Jan. 22, 2009.

(51) Int. Cl.
| | |
|---|---|
| *B02C 17/18* | (2006.01) |
| *A61L 11/00* | (2006.01) |
| *B02C 25/00* | (2006.01) |
| *B02C 19/18* | (2006.01) |
| *A61L 2/07* | (2006.01) |

(52) U.S. Cl.
CPC . *A61L 11/00* (2013.01); *A61L 2/07* (2013.01); *B02C 19/186* (2013.01); *B02C 25/00* (2013.01)

(58) Field of Classification Search
CPC .............................. B02C 25/00; B02C 19/186
USPC .......................................... 241/23, 33, 34, 36
See application file for complete search history.

(56) References Cited

U.S. PATENT DOCUMENTS

| | | | |
|---|---|---|---|
| 5,190,226 A | 3/1993 | Holloway | |
| 5,253,764 A | 10/1993 | Gement | |
| 5,361,994 A | 11/1994 | Holloway | |
| 5,407,809 A | 4/1995 | Finn | |
| 5,427,650 A | 6/1995 | Holloway | |
| 5,540,391 A | 7/1996 | Anderson | |
| 5,636,449 A | 6/1997 | Gaddis et al. | |
| 5,655,718 A | 8/1997 | Anderson | |
| 6,397,492 B1 | 6/2002 | Malley | |
| 7,347,391 B2 | 3/2008 | Michalek et al. | |
| 7,584,911 B2 * | 9/2009 | Michalek et al. | ............... 241/23 |
| 2008/0061173 A1 * | 3/2008 | Michalek et al. | ............... 241/47 |
| 2008/0217444 A1 | 9/2008 | Michalek et al. | |

* cited by examiner

*Primary Examiner* — Faye Francis
(74) *Attorney, Agent, or Firm* — Standley Law Group LLP

(57) ABSTRACT

The present invention is a method and apparatus for controlling the processing solid waste material in a vessel during a processing cycle, including: (1) loading the vessel with a charge of solid waste products, said vessel including: (a) a rotatably mounted cylindrical vessel having an interior surface and two ends, at least one end terminating in a hatch that may be opened to allow access to the interior of said vessel and sealably closed to allow pressurization of said vessel; (b) a vessel steam inlet for injecting steam into at least one of said ends so as to come into contact with waste material placed into said vessel; (c) a thermometer adapted to monitor the processing temperature of the waste material placed into said vessel during an operational cycle; (d) a timer adapted to monitor the processing time of an operational cycle for the waste material placed into said vessel; (e) a microprocessor having processing instructions adapted to calculate the required processing time by integrating the function of the said processing temperature versus the processing time so as to be able to determine whether a predetermined energy input to the waste material has been attained, and to issue a signal in response thereto; and (2) terminating said processing cycle in response to said signal.

3 Claims, No Drawings

METHOD AND APPARATUS FOR TREATING WASTE INVOLVING CONTROL OF ENERGY INPUT TO ASSURE STERILIZATION

RELATED APPLICATION DATA

This application claims the priority benefit of U.S. Provisional Application Ser. No. 61/205,632, filed Jan. 22, 2009, which is hereby incorporated in its entirety herein by reference.

TECHNICAL FIELD

The present invention relates to the treatment of municipal solid waste and the like. This invention disclosure presents a means of controlling an autoclave and utilizing steam to treat solid waste inside a rotating vessel.

BACKGROUND AND SUMMARY OF THE INVENTION

The present invention relates to systems and methods for treating process material and, more particularly, to systems and methods for treating municipal solid waste material, medical waste material, reclaimed paper and the like.

This process typically involves sterilizing high density materials such as glass, plastics, metals and recovering others from municipal solid waste (MSW) and converting paper, cardboard, food waste, etc. to a usable fiber and separating it from other recyclable materials.

As a result of increasing scarcity of landfills and more stringent environmental regulations, efforts have been made to reduce the volume of process material, such as municipal solid waste (MSW) and paper material, such as newsprint and other reclaimed and recycled paper products as a step in the process of disposing of the material, either by depositing it in landfills, incinerating it or recycling it.

Systems and methods have been developed to break down such material for disposal, or in the case of paper products, use as insulation, or for further processing to produce a combustible product.

A waste autoclave is a form of solid waste treatment that utilizes heat, steam and pressure of an industrial autoclave in the processing of waste. Saturated steam is pumped into the autoclave at elevated temperatures. The pressure in the vessel is maintained at for a temperature-dependant period to allow the process to fully 'cook' the waste. The autoclave process gives a very high pathogen and virus kill.

The 'cooking' process causes plastics to soften and flatten, paper and other fibrous material to disintegrate into a fibrous mass, bottles and metal objects to be cleaned, and labels etc. to be removed.

Rotating waste autoclaves provide mechanical forces to further process the waste. With rotation, the cellulose fibers (in paper, cardboard, and yard wastes) are mechanically and thermally pulped, analogous to the process known as thermo-mechanical pulping in the pulp and paper industry.

After 'cooking', the steam flow is stopped and the pressure vented. When depressurized, the autoclave door is opened, and by rotating the drum the 'cooked' material can be discharged and safely and easily separated by a subsequent series of screens and recovery systems. Consequently, a waste autoclave system can serve as a functional alternative to landfills, providing benefits of recycling of clean and sterile materials recovered from municipal wastes.

A basic invention for municipal waste autoclaves is found in U.S. Pat. No. 4,540,495 (Holloway, 1985) and is now in the public domain. This application describes inventions that improve the functionality of waste autoclave systems.

The present invention accordingly represents an improvement over prior art apparatus and methods, such as those described in U.S. Pat. Nos. 5,540,391; 5,126,363; 5,253,764; 5,190,226; 5,361,994; 5,427,650; 5,407,809; 5,636,449; 5,655,718; 6,397,492, and 7,347,391, all of which are incorporated herein by reference. PCT application PCT/US06/16773 and co-pending patent application Ser. No. 11/716,101 are also hereby incorporated herein by reference. Autoclaves generally require substantial "overcooking" to assure that the heterogenous materials in the autoclaves are properly treated. Hospital autoclaves, for example, typically use either a vacuum to remove air, or cautiously use density gradients to allow the removal of cool air as hot steam is introduced . . . both methods to provide some assurance that the contents are all exposed to steam. Further, test strips are also used to confirm that the (preset) cooking cycle achieves the desired organism kill.

Rotating waste autoclaves eliminate some of difficulties of heterogeneous materials by tumbling and comminution of the waste components. However, municipal waste is highly heterogeneous in nature. Single vessel components, for example, might include a large box of frozen food that has been insulated by paper, and/or a mass of putrescible waste rolled up in a carpet.

While the mechanical processes of a waste vessel help in assuring that the waste components each receive proper treatment, to date vessel systems have specified a long-duration fixed-duration cooking cycle in order to provide such assurances. Fixed-time cooking cycles will either under-treat or over-treat wastes, and neither outcome is desirable.

In a co-pending patent application Ser. No. 11/981,144 (and hereby incorporated herein by reference), there is disclosed a method for time-tracking of temperature contents in order to allow the treatment system to achieve an overall goal of a desired kill fraction. The system of the present invention as described herein provides a systematic process to assure that the various components of the vessel load each achieve a desired treatment level.

In essence, the vessel of the present invention may include the provision of a multiplicity of content temperature monitoring sites, such as thermocouple wells. The term thermocouple well is used henceforth, but it conceptually includes all temperature monitoring equipment.

The multiplicity of sites allows the temperature to be determined at a number of points, both circumferentially and longitudinally. A control system is provided to track the temperature (and the rate of change of temperature) at each of these thermocouple wells.

Variations between wells are signals that the waste treatment provided is not yet uniformly received by the non-homogenous wastes. The decision point to terminate the process is developed when the signals from the array of thermocouple wells are in agreement. The control system is provided with adaptive programming so that equipment biases between the various thermocouple wells, and or individual thermocouple failures, can be factored out of the decision process.

SUMMARY OF THE INVENTION

In general terms, the invention includes an apparatus, system, waste treatment facility and method of autoclave operation and waste treatment.

The present invention includes a method of controlling the processing solid waste material in a vessel during a processing cycle, comprising: (1) loading the vessel with a charge of solid waste products, said vessel comprising: (a) a rotatably mounted cylindrical vessel having an interior surface and two ends, at least one end terminating in a hatch that may be opened to allow access to the interior of said vessel and sealably closed to allow pressurization of said vessel; (b) a vessel steam inlet for injecting steam into at least one of said ends so as to come into contact with waste material placed into said vessel; (c) a thermometer adapted to monitor the processing temperature of the waste material placed into said vessel during an operational cycle; (d) a timer adapted to monitor the processing time of an operational cycle for the waste material placed into said vessel; (e) a microprocessor having processing instructions adapted to calculate the required processing time by integrating the function of the said processing temperature versus the processing time so as to be able to determine whether a predetermined energy input to the waste material has been attained, and to issue a signal in response thereto; and (2) terminating said processing cycle in response to said signal.

The microprocessor's instructions that are adapted to calculate the required processing time by integrating the function of the said processing temperature versus the processing time so as to be able to determine whether a predetermined energy input to the waste material has been attained, may be provided by any computer programming instructions that provide the required calculations be made with the processing temperature versus the processing time. This may be done through the use of sensor outputs and according digital readers and converters, as are known and used in the art, for use with computer program inputs and languages.

The processing instructions typically and preferably are adapted to maintain said processing temperature above 280 F. degrees, although it is preferred that the vessel be operated in the range of 300-334 F. a range which is as high as possible without degrading the plastics in the processed waste. However, the upper temperature may be increased in the absence of plastic in the waste. Overall, the accuracy of thermocouple signals increases with temperature difference.

The processing instructions are adapted to achieve a predetermined energy input adapted to provide an assured kill of at least one pathogen selected from the group consisting of Chronic wasting disease, Bovine spongiform encephalopathy (Mad Cow Disease), and Human's CJD (kuru) disease pathogens. The assured kill energy input for each of these organisms is either known or may be obtained without undue experimentation.

The invention also includes an apparatus for treating solid waste and for controlling its processing during a processing cycle, comprising: (a) a rotatably mounted cylindrical vessel having two ends, at least one end terminating in a hatch that may be opened to allow access to the interior of said vessel and sealably closed to allow pressurization of said vessel; (b) a vessel steam inlet for injecting steam into said vessel so as to come into contact with waste material placed into said vessel; (c) a thermometer adapted to monitor the processing temperature of the waste material placed into said vessel during; (d) a timer adapted to monitor the processing time for the waste material placed into said vessel; (e) a microprocessor having processing instructions adapted to calculate the required processing time by integrating the function of the said processing temperature versus the processing time so as to be able to determine whether a predetermined energy input to the waste material has been attained, and to issue a signal in response thereto; and to terminate said processing cycle in response to said signal.

The preferred processing instructions are as described above.

The present invention also includes a waste treatment facility containing the apparatus of the present invention.

DETAILED DESCRIPTION OF THE PREFERRED EMBODIMENTS

In accordance with the foregoing summary, the following provides a detailed description of the preferred embodiment, which is presently considered to be the best mode thereof.

The present invention includes a waste treatment autoclave wherein the achievement of thermal equilibrium inside of the vessel can be determined by an accurate and repeatable test method, and the results recorded.

The waste treatment autoclave preferably comprised of a series of longitudinal and radially disperse thermocouples arranged to sense temperatures near the surface inside the autoclave. The thermocouples may be randomly distributed in both axes.

It is preferred that the autoclave is caused to rotate and/or tilt for the purposes of mixing, comminution, pulping, and other purposes.

The preferred vessel temperature range is at least 320 degrees, preferably between 320 and 334F, for the purpose of increasing the reliability of the thermocouple signals.

The autoclave control system includes monitors in the temperature field, and is adapted to actively control the cooking process based upon, in part, achieving a uniform temperature in both three dimensional space and time inside the vessel. This is done though the array of monitors array about the waste mass along the dimensions of the autoclave. The cooking process may be controlled in any number of ways such as through control of steam input, etc., using methods and apparatus as is known and used in the field.

Preferably the system includes a control system that monitors the temperature field, and actively controls the cooking process based upon, in part, achieving a uniform temperature profile in three dimensional space and time inside the vessel, and wherein the control system provides an electronic record of the temperature history, thus allowing a certification of the results of the vessel autoclave treatment.

It is also preferred that the system includes a control system that actively adjusts its decision process as thermocouples age and fail.

What is claimed is:
1. A method of controlling the processing of a solid waste material in a vessel during a processing cycle, comprising the steps of:
  loading a charge of the solid waste material into an inlet of the vessel:
  injecting pressurized steam into the vessel;
  monitoring an internal temperature of the vessel as a function of time during the processing cycle and storing the temperature and time data in a processor;
  determining, in the processor, an energy input to the vessel by calculating an integral of the internal temperature with respect to time from the stored data;
  comparing, in the processor, the determined energy input to a predetermined energy input; and
  providing a signal from the processor when the determined energy input exceeds the predetermined energy input.
2. The method of claim 1, wherein:
  the pressurized steam maintains the internal temperature above 280 degrees F.

3. The method of claim 2, wherein:
the predetermined energy input is selected to provide an amount of energy sufficient to provide an assured kill of at least one pathogen selected from the group consisting of: chronic wasting disease, bovine spongiform encephalopathy and human CJD (kuru) disease.

\* \* \* \* \*